United States Patent [19]
Sagi et al.

[11] 3,936,482
[45] Feb. 3, 1976

[54] ORGANO TIN COMPOUNDS USEFUL AS CATALYSTS IN THE POLYCONDENSATION OF ORGANOSILICON COMPOUNDS

[75] Inventors: Ferenc Sagi, Bron; Michel Roussos, Lyon, both of France

[73] Assignee: Rhone-Poulenc, S.A., Paris, France

[22] Filed: Apr. 29, 1974

[21] Appl. No.: 465,075

Related U.S. Application Data

[62] Division of Ser. No. 237,514, March 23, 1972, Pat. No. 3,819,673.

[52] U.S. Cl. ................... 260/429.7; 260/448.2 E
[51] Int. Cl.² ............................................ C07F 7/22
[58] Field of Search ............................... 260/429.7

[56] References Cited
UNITED STATES PATENTS

| | | | |
|---|---|---|---|
| 2,752,325 | 6/1956 | Leistner et al. | 260/429.7 X |
| 2,872,468 | 2/1959 | Leistner et al. | 260/429.7 |
| 3,115,509 | 12/1963 | Mack | 260/429.7 |
| 3,524,831 | 8/1970 | Stapfer | 260/429.7 X |

*Primary Examiner*—Helen M. S. Sneed
*Attorney, Agent, or Firm*—Stevens, Davis, Miller & Mosher

[57] ABSTRACT

Organothio-tin compounds of the general formula

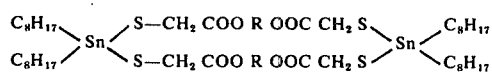

in which R represents a p-xylylene radical or a

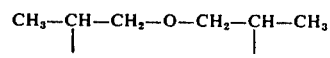

radical, useful as catalysts in the polycondensation of organosilicon compounds, are prepared by reacting a di-octyl tin oxide with the diester obtained by reacting thioglycollic acid with 2,2'-dihydroxy-dipropyl ether or p-xylylene glycol.

3 Claims, No Drawings

ORGANO TIN COMPOUNDS USEFUL AS CATALYSTS IN THE POLYCONDENSATION OF ORGANOSILICON COMPOUNDS

This is a division of application Ser. No. 237,514 filed Mar. 23, 1972, now U.S. Pat. No. 3,819,673.

The present invention provides a process for the polycondensation of organosilicon compounds in the presence of certain tin compounds.

The tin compounds used in the process of the invention are cyclic organothiotins corresponding essentially to the following formula

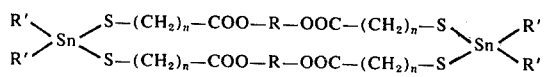

in which the symbols R, which may be the same or different, each represent a divalent hydrocarbon radical, or a divalent radical consisting of divalent hydrocarbon radicals bonded to one another by —O—, —CO—, —COO— or —CHOH— radicals, the symbols R', which may be the same or different, each represent a monovalent hydrocarbon radical and n represents a positive integer.

The organo-tin compounds of formula I can also contain products of the following formulae

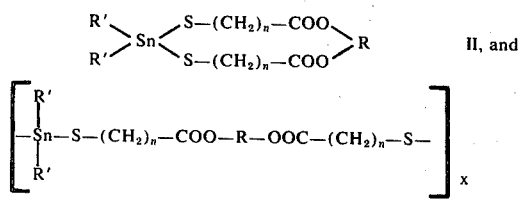

in which x represents an integer, the formula III compound apparently being in equilibrium with the formula I compound. The presence of small amounts of the formula II and III compounds, e.g. up to about 5% does not appear to modify the catalytic activity of the organothiotin compound of the formula I.

In the compounds of formulae I, II and III the symbol R can, for example, represent an alkylene radical such as those with 2 to 13 carbon atoms, an arylene radical, such as phenylene, biphenylene, xylylene or

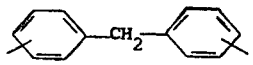

or one of the above mentioned radicals substituted by one or more alkyl, aryl, cyclohexyl or alkoxy radicals; R can also represent a polyoxyalkylene radical, particularly a polyoxyethylene or polyoxypropylene radical, or a —R''—O—R''— radical in which R'' represents an alkylene or arylene radical, for example, one of those specifically mentioned above.

Specific examples of symbol R are those where the diol HO—R—OH is 1,2-ethanediol; 1,3-propanediol; 1,2-propanediol, 1,2-butanediol; 1,3-butanediol, 1,4-butanediol; 2,3-butanediol; catechol, resorcinol, hydroquinone and their derivatives substituted on the benzene ring, as for example, 3,5-dimethylcatechol, 2,5-dimethylhydroquinone, 2,2'-dihydroxy-diphenyl, 3,3' -dihydroxydiphenyl, 4,4' -dihydroxy-diphenyl, phenylhydroquinone, 4-phenyl-pyrocatechol and their derivatives substituted on the benzene rings; 3,3'-dihydroxy-diphenylmethane; 4,4'-dihydroxy-diphenylmethane and their derivatives substituted on the benzene rings; hydrobenzoin, phenyl-ethylene glycol, benzopinacol, diethylene glycol, triethylene glycol, dipropylene glycol, o-xylene glycol m-xylene glycol, p-xylene glycol, 2,2'-dihydroxy-dipropyl ether, 3,3'-dihydroxy-dipropyl ether and 4,4'-dihydroxydibutyl ether.

The symbol R' can represent an alkyl radical with 1 to 20 carbon atoms, an alkenyl radical with 2 to 20 carbon atoms or an aryl or aralkyl radical such as methyl, ethyl, butyl, n-octyl, iso-octyl, myricyl, phenyl, tolyl, vinyl, allyl, benzyl and menyl radicals. In practice however, radicals with 4 carbon atoms to 12 carbon atoms are preferred.

The value of n is usually 1 to 18, and is preferably 1 to 4.

The silicon compounds which can be polycondensated in the presence of the derivatives of the formula I should contain at least an Si—OH group. They can contain other types of functional groups (Si—X) which react with water to give Si—OH groups, or which react with the Si-OH groups to form Si—O—Si bonds with elimination of HX. Thus, a silicon compound containing Si—X groups will be mixed with the formula I catalyst. By exposing the mixture to humidity, the hydrolysis of the Si—X groups will produce Si—OH groups, the condensation of which will be accelerated by the presence of the catalyst.

The symbols X can represent hydrogen, alkoxy groups such as methoxy, ethoxy or —O—CH$_2$—CH$_2$—OCH$_3$, acyloxy groups such as acetoxy, propionyloxy or benzyloxy, and ketoxime groups such as —O—N=C(CH$_3$)$_2$; aldoxime groups such as —O—N=CH—CH$_3$; carbamate groups such as

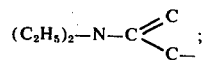

R$_2$''N—O— groups where R'' is a methyl, ethyl or phenyl radical; and halogen atoms such as Cl, Br and F as well as any hydrolysable group attached to the silicon atom.

There are between 0.9 and 3 other substituent groups on each atom of the silicon reactant. They can be hydrocarbon radicals, for example, alkyl radicals such as methyl, ethyl and propyl radicals, alkenyl radicals such as vinyl, allyl or hexenyl radicals, cycloalkyl radicals such as cyclohexyl, cyclopentyl and methylcyclohexyl radicals, cycloalkenyl radicals such as cyclohexenyl, aryl radicals such as phenyl, tolyl, xenyl and xylylenenaphthyl radicals, and aralkyl radicals such as benzyl and phenylethyl radicals.

They may also be halogenated hydrocarbon radicals such as chloromethyl, γ-chloropropyl, bromooctadecyl, chlorophenyl, fluorocyclohexyl, chlorobutenyl, α,α,α-trifluorotolyl and 3,3,3-trifluoro-propyl radicals. They may also consist of hydrocarbon chains linked by —O—, —COO—, —CO— or —CHOH— radicals, such as —(CH$_2$CH$_2$O)$_7$CH$_3$, —(CH$_2$)$_3$—O Et, —(CH$_2$)$_3$—OOC—CH=CH$_2$, —(CH$_2$)$_6$—OOC—Me and —(CH$_2$)$_2$COO Et; they can also be hydrocarbon radicals susbstituted by —CH, —NH$_2$, —CONH$_2$ or —SH radicals such as —(CH$_2$)$_2$CH, —(CH$_2$)$_3$CN and —C$_6$H$_4$—CH.

The organosilicon compounds have different structures combining species of the type R Si O$_{3/2}$, R$_2$SiO and R$_3$SiO$_{1/2}$. The atoms of silicon can also be linked among themselves by atoms or radicals other than oxygen, such as divalent radicals, e.g. methylene, dimethylene, hexamethylene and phenylene or hydrocarbon ether radicals such as $-C_6H_4-O-C_6H_4-$, or with silazane links e.g. Si—NH—Si or $$Si-N-Si;$$
$$\phantom{Si-}|\phantom{-Si}$$
$$CH_3$$

or with Si—S—Si links.

Certain of the organothiotin compounds of the formula I, as well as their method of preparation, have already been described in German patent specification No. 1,020,335. They can be obtained by the reaction of a ω,ω'-dithiodiester with a di(organo)-tin oxide, the ω,ω'-dithioester being itself obtained by the diesterification of a glycol by a ω-thioalkanoic acid.

Other organothiotin compounds of formula I are new compounds and these new compounds from a further aspect of the present invention. The new compounds are those of formula I where each R' is a $C_8H_{17}$ radical, R is a p-xylylene radical or a $$CH_3-CH-CH_2-O-CH_2-CH-CH_3$$
$$\phantom{CH_3-CH}|\phantom{-CH_2-O-CH_2-CH}|\phantom{-CH_3}$$

radical and $n = 1$.

The new compounds may be prepared by a method analogous to the known method, that is by reacting a di-octyl tin oxide with the diester obtained by reacting thioglycollic acid with 2,2'-dihydroxy-dipropyl ether or p-xylylene glycol.

The organothiotin compounds of formula I show a remarkable catalytic activity, superior to that of the tin derivatives already used, are storage stable and stable when used under exceptional conditions.

Their high activity allows them to be used in smaller amounts, in comparison to the tin catalysts previously used, to achieve an equivalent final result. If they are used in equivalent amounts to the amounts used hitherto, then a more rapid catalysis results or a lower catalysis temperature can be used. Their stability allows their use as aqueous emulsions for catalysing the polycondensation of organosilicon compounds in emulsion.

The catalysts used in the present invention can be used under the same conditions as the tin catalysts used hitherto in the polycondensation, such as diorganotin dialkanoates. Thus the concentration of catalyst can vary between 0.01 and 3% expressed as the weight of tin relative to the silicon derivatives used and the polycondensation temperature can be 15° to 200°C.

Examples 1 and 2 illustrate the product of novel compounds of formula I while the subsequent Examples illustrate the polycondensation process of the invention.

EXAMPLE 1

368 g. (4mols) of thioglycollic acid $HS-CH_2-COOH$, (as an 80% strength aqueous solution), 281 g. (2.1 mols) of 2,2'-dihydroxy-dipropyl ether and 200 g. of toluene are introduced into a flask equipped with a stirrer.

The flask is heated to reflux the toluene for 2 hours during which time about 80% of the theoretical amount of water produced in the reaction is removed azeotropically. To complete the esterification, 3.2 g. of para-toluenesulphonic acid are added, and after 3 hours of reaction, practically all the theoretical amount of water formed by the esterification reaction can be removed.

The toluene solution is cooled to about 20°C, washed three times with 100 cm³ of an aqueous solution containing 5% of $NaHCO_3$, and then twice with 100 cm³ of pure water. The organic phase is then dried over anhydrous sodium sulphate and filtered.

636 g. of a solution containing 508 g. of the desired ester (theory 564 g.) corresponding to the formula $$\phantom{HS-CH_2-COO-}CH_3\phantom{-CH_2-O-CH_2-}CH_3$$
$$\phantom{HS-CH_2-COO-}|\phantom{-CH_2-O-CH_2-}|$$
$$HS-CH_2-COO-CH-CH_2-O-CH_2-CH-OOC-CH_2-SH$$

are obtained.

483 g. of the solution obtained above, 520 g. of di-n-octyl-tin oxide $[O\,Sn\,(C_8H_{17})_2]$ and 400 g. of toluene are introduced into a flask equipped with a stirrer.

The mixture is boiled for 10 hours during which time 17.5 g. of $H_2O$ are removed azeotropically. After cooling, the product is filtered to remove 1.4 g. of residue which had not reacted. The filtrate is washed twice with 250 cm³ of an aqueous solution containing 5% of $NaHCO_3$, and then twice with 250 cm³ of pure water. The toluene solution thus obtained is dried over anhydrous $Na_2SO_4$. It weights 1,085 g. is straw yellow in colour and contains 670 g. of the desired organo-tin derivative corresponding principally to the formula $$\phantom{C_8H_{17}\diagdown\phantom{Sn}\diagup S-CH_2-COO-}CH_3\phantom{-CH_2-O-CH_2-}CH_3$$
$$C_8H_{17}\diagdown\phantom{Sn}\diagup S-CH_2-COO-CH-CH_2-O-CH_2-CH-OOC-CH_2-S\diagdown\phantom{Sn}\diagup C_8H_{17}$$
$$\phantom{C_8H_{17}\diagdown}Sn\phantom{\diagup S-CH_2-COO-CH-CH_2-O-CH_2-CH-OOC-CH_2-S\diagdown}Sn$$
$$C_8H_{17}\diagup\phantom{Sn}\diagdown S-CH_2-COO-CH-CH_2-O-CH_2-CH-OOC-CH_2-S\diagup\phantom{Sn}\diagdown C_8H_{17}$$
$$\phantom{C_8H_{17}\diagup\phantom{Sn}\diagdown S-CH_2-COO-}|\phantom{-CH_2-O-CH_2-}|$$
$$\phantom{C_8H_{17}\diagup\phantom{Sn}\diagdown S-CH_2-COO-}CH_3\phantom{-CH_2-O-CH_2-}CH_3$$

The tin content is 17.95% of the dry product, theoretical: 19.05%. The molecular weight is 1,020 ± 5o (osmometry), theoretical = 1250.

EXAMPLE 2

1 Mol (138 g.) of p-xylylene glycol, 2.1 mols (193 g.) of thioglycollic acid (in the form of an 80% strength aqueous solution) and 400 g. of toluene are introduced into a stirred flask.

Using the same procedure as described in Example 1,487 g. of solution containing 257 g. of the diester of the formula $$HS-CH_2-COO-CH_2-\!\!\!\left\langle\!\!\!\bigcirc\!\!\!\right\rangle\!\!\!-CH_2-OOC-CH_2-SH$$

are finally obtained.

Analysis shows that the molecule contains 20.7% of SiH, theoretical 23.1%. Alcohol groups cannot be detected by infra-red methods.

400 g. of the toluene solution obtained above, 280 g. of di-n-octyl-tin oxide and 200 g. of toluene are introduced into a stirred flask. Using the same procedure as described in Example 1, 630 g. of a toluene solution containing 430 g. of the organo-tin derivative corresponding principally to the formula

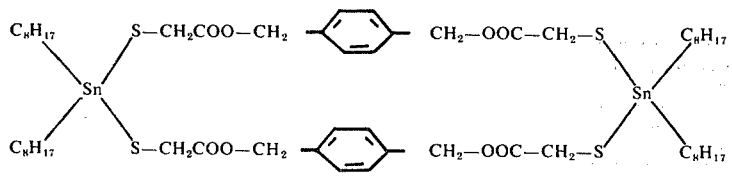

are obtained.

The tin content of the dry product is 17.9%, theoretical = 18.9%. Residual SH <1%.

EXAMPLE 3

This Example shows the stability of the catalysts of formula I and of their catalytic power.

An emulsion A of the catalyst is prepared by mixing an organic solution containing:

43 g. of the toluene solution of Example 1 containing: 17.95% of Sn,
150.4 g. of zinc octoate containing 12% of zinc, diluted with 150.4 g. of toluene,
23.2 g. of toluene, and
23.2 g. of perchloroethylene,
with an aqueous solution consisting of: 11.3 g. of a polyvinyl alcohol known by the name Rhodoviol 13/135 P and 100.0 g. of water.

The mixture is homogenised in a colloid mill and the resulting emulsion adjusted to a Sn content of 1% by the addition of 130 g. of water.

An emulsion B is prepared according to the same technique by adding the quantity of catalyst of Example 2 required to give 1% of Sn.

Emulsion C is prepared by replacing the catalysts of the invention by an equivalent amount of Sn in the form of di-n-octyl tin diacetate.

Emulsion D is prepared using the equivalent amount of Sn in the form of di-n-butyl tin diacetate.

A silicone emulsion, intended for the non-stick treatment of paper, is prepared by mixing 252 g. of a dimethylpolysiloxane with terminal —OH groups, and of viscosity 30 cPo at 25°C, 80 g. of a 50/50 by volume mixture of toluene and perchloroethylene and 180 g. of the aqueous solution of Rhodoviol prepared as above.

The silicone emulsion is produced in a colloid mill, and then adjusted to a silicone content of 40% by the addition of 168 g. of water.

25 parts by weight of the silicone emulsion, 5 parts of the catalyst emulsion A, B, C or D, and the water necessary to bring the total volume to 200 cm³ are mixed together. The resulting catalysed emulsion is applied to paper by means of a glass rod. After drying the treated paper at 120°C for 2 minutes, the silicone is polycondensed. A determination shows that approximately 0.7 g. of active silicone matter remains per $m^2$ of paper.

A similar treatment of paper is carried out with the the catalysed diluted emulsions mentioned above, but after they have first undergone a natural aging of 6 hours.

The papers treated in this way are subjected to a self-adhesion test by applying an adhesive tape, known under the name Sparadrap, to the paper and by measuring the force necessary (in g./cm) to remove the tape by pulling at an angle of 180°. The removed tape is then applied to a steel sheet and the force necessary to detach it from the steel sheet is measured. Finally the force necessary to detach an adhesive tape which has not undergone contact with the silicone paper and which has been directly applied to the steel sheet is measured.

This last measurement will be designated by the term "standard adhesion"; the detachment from the paper will be designated: the non-stick character; the detachment from the steel sheet after contact of the tape with paper will be designated: the subsequent adhesion. The results obtained are given in Table I below. The quality of the silicone treatment of the paper will be the higher the lower is the non-stick character and the closer is the lower is the non-stick character and the closer is the subsequent adhesion to the standard adhesion.

TABLE I

| Catalysts | Fresh catalyst emulsion | | | Catalyst emulsion aged for 6 hours | | |
|---|---|---|---|---|---|---|
| | Standard | Non-stick character | Subsequent adhesion | Standard | Non-stick character | Subsequent adhesion |
| A | 167 | 12 | 167 | 157 | 15 | 150 |
| B | 172 | 9 | 170 | 171 | 13 | 165 |
| C | 170 | 10 | 154 | 163 | 15 | 145 |
| D | 165 | 12 | 150 | 165 | 15 | 143 | methylpolysiloxane in which about 50% of the chain ends are OH groups and 50% are $OCH_3$ groups, and which has a viscosity at 25°C of 2,000 cPo, 9.2 g. of a methylhydrogenopolysiloxane, the chain ends of which are $(CH_3)_3 SiO_{1/2}$ and containing 36.5% of SiH, 34 g. of The good performance of the papers treated with the emulsion catalysed with the catalysts A and B can thus be seen. Catalysts C and D, give a weak subsequent adhesion; this demonstrates a migration of the silicone from the treated paper to the adhesive tape, and thus a loss of adhesion to the latter.

EXAMPLE 4

The same tests are repeated by treating the papers as described in Example 3, but the curing of the silicone is carried out only at 80°C for 30 seconds. The results of the tests are given in the following Table II below.

TABLE II

| Cata- lysts | Fresh catalyst emulsion | | | Catalyst emulsion aged for 6 hours | | |
|---|---|---|---|---|---|---|
| | Stan- dard | Non- stick character | Subsequent adhesion | Stan- dard | Non- stick character | Subsequent adhesion |
| A | 170 | 18 | 168 | 170 | 18 | 165 |
| B | 172 | 20 | 172 | 172 | 18 | 167 |
| C | 168 | 25 | 145 | 170 | 28 | 145 |
| D | 170 | 27 | 140 | 170 | 30 | 150 |

These curing conditions show that the reactivity of the catalyst emulsions A and B is still adequate for them to provide the desired properties, whilst emulsions C and D have a less pronounced non-stick character and give too great a migration of the silicone of the paper to the adhesive.

EXAMPLE 5

A solution is prepared of 28 parts of a dimethylsiloxane rubber, the chain ends of which are blocked by CH groups and the Williams plasticity of which is 150, 2 parts of a methylhydrogenopolysiloxane, the chain ends of which are blocked by $(CH_3)_3 SiO_{1/2}$ groups and the Si—H content of which is 47% by weight, and 70 parts of toluene.

Solutions E, F and G to be used in treating papers, are prepared as follows:

To 34 g. of the above mentioned solution are added 0.38 g. of the solution of Example 1, 0.10 g. of acetic acid and 166.0 g. of oil C (petroleum fraction boiling between 72 and 98°C). The resulting solution is designated solution E.

In the same way, a solution F in which the tin catalyst is replaced by the solution of Example 2 is prepared. Finally, in the same way, a solution G is prepared in which the tin catalyst is di-n-butyl-tin dilaurate, containing an equivalent amount of Sn.

Using these solutions, the silicone is applied to the paper by means of a glass rod. After drying the treated paper at 120°C. for 2 minutes, the silicone is polycondensed. A determination shows that about 0.4 g. of active material remains per $m^2$ of paper.

This paper is subjected to the same tests as those described in Example 3 and the results are given in Table III below.

TABLE III

| Solutions | Standard | Non-stick character | Subsequent adhesion |
|---|---|---|---|
| E | 165 | 6 | 163 |
| F | 172 | 8 | 165 |
| G | 168 | 19 | 150 |

This table shows that at a constant proportion of tin relative to the silicone, the catalysis is more effective with the catalysts of the invention (solutions E and F).

EXAMPLE 6

The procedure described in Example 5 is repeated but the paper is dried only at 80°C for 30 seconds. The results of the tests are given in Table IV.

TABLE IV

| Solutions | Standard | Non-stick character | Subsequent adhesion |
|---|---|---|---|
| E | 158 | 9 | 150 |
| F | 172 | 13 | 167 |
| G | 170 | 36 | 148 |

This table shows that with the solutions E and F, the catalysis is still very adequate, although with the solution G, the non-stick character becomes mediocre and the migration of the insufficiently catalysed silicone becomes too great.

EXAMPLE 7

In this example, the catalysts are used for curing a non-stick silicone resin. It is difficult to estimate the non-stick character of a silicone coating on a solid support, because the choice of adhesive material must show a sufficient "grab" to limit the number of measurements within a suitable time. It must nevertheless permit sufficient measurement to represent as well as possible the permanent use to which the silicone will be submitted.

The test described here consists of cooking omelettes, which have been salted and peppered, on a metallic support, previously coated with a cured silicone coating. The silicone composition used in the coating is the following: 3.1% by weight of a methylphenylpolysiloxane resin containing 4% by weight of OH groups bonded to the silicon; 0.55 phenyl group per silicon and 1.35 phenyl and methyl groups per silicon; 0.01% of the monethyl ether of dipropylene glycol; 0.20% of dimethylpolysiloxane fluid, the chain ends of which are blocked by OH- groups, proportion of OH: 4.2%; 1.79% of methyltriacetoxysilane and 94.90% of 1,1,1-trichloroethane.

Various samples of this resin are catalysed with the tin salts shown below so that there is 0.27% by weight of catalyst relative to the resin described above. In this case, the less tin the active molecule contains, the less of it calculated as metal is present.

Resin 1 contains the catalyst of Example 1,
Resin 2 contains the catalyst of Example 2,
Resin 3 dilaurate, contains di-n-butyl-tin dilaurate,e
Resin 4 contains d-n-butyl-tin diacetate,
Resin 5 contains di-n-octyl-tin diacetate and
Resin 6 contains di-n-octyl-tin dilaurate.

Each catalysed composition is placed in a closed glass container. Each is tested immediately after catalysis and after storage for 6 months.

The catalysed resins thus obtained are applied to aluminium egg pans, of 12 cm diameter. These pans are previously carefully degreased, then coated with the catalysed resins. The solvent is evaporated in about 15 minutes and the resin is finally cured by stoving at 150°C. for 30 minutes.

The eggs are beaten, salted and peppered. No greasy matter whatsoever is used. The pen is heated on a Bunsen burner thus allowing a temperature of 250°C to be reached on the treated face. 10 cm³ of beaten eggs are deposited, left to cook for 1 minute and the resulting omelette is removed with a wooden spatula. The pan is rapidly cooled by placing it on a cold metallic body. The treated face is then at about 80°C. after 1.5 minutes. The pan is heated again to 250°C. and the operation is begun again. After every 20 omelettes the pan is allowed to cool to about 20°C. and the cycle is repeated.

Table V below shows the number of omelettes that can be cooked and removed from the pan without sticking to the surface.

TABLE V

| Resin No. | 1 | 2 | 3 | 4 | 5 | 6 |
|---|---|---|---|---|---|---|
| Number of omelettes with the fresh catalyst | >80 | >80 | 36 | 30 | 37 | 40 |
| Number of omelettes with the catalyst aged for 6 months | >80 | >80 | 33 | 25 | 31 | 34 |

With resins 1 and 2, the number of omelettes made is in excess of 80, the test having been stopped at this value. The other resins do not begin even to approach this number. Thus with resin No. 3 for example, sticking begins at the 36th omelette and, if the test is continued a little longer until the 42nd omelette, it becomes practically impossible to separate the omelette from the pan.

It is also noteworthy that the efficacy is maintained at a high level with the resins stored for 6 months in the cases of No. 1 and No. 2, in accordance with the invention; in cases 3, 4, 5 and 6 the efficacy has diminished, compared to that of the freshly catalysed resin.

EXAMPLE 8

The same tests are repeated, this time catalysing the silicone resin with a constant proportion of tin, the tin being supplied by the catalysts already described in Example 7.

The concentration of tin is 1% by weight relative to the quantity of active silicone matter. It is then noted that the efficacy of the resins containing the catalysts of the invention always remains superior to that of the resins containing the tin compounds used hitherto.

We claim:

1. Organothio-tin compounds of the general formula

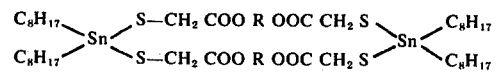

in which R represents a p-xylylene radical or a

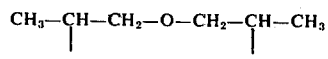

radical.

2. The organo-tin compound of claim 1 which has the formula:

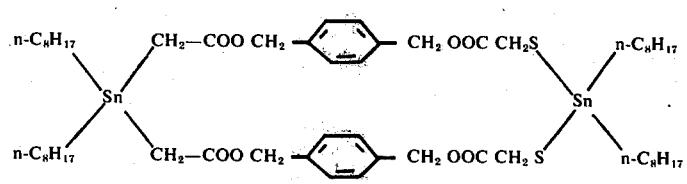

3. The organo-tin compound of claim 1 which has the formula

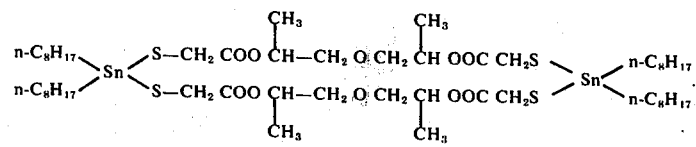

* * * * *

UNITED STATES PATENT OFFICE
CERTIFICATE OF CORRECTION

Patent No. 3,936,482  Dated February 3, 1976

Inventor(s) Ferenc SAGI and Michel ROUSSOS

It is certified that error appears in the above-identified patent and that said Letters Patent are hereby corrected as shown below:

After "[21] Appl. No.: 465,075" and before "Related U.S. Application Data", please insert the following:

--Foreign Application Priority Data

March 24, 1971 France..........71/10383.--

Signed and Sealed this

Ninth Day of November 1976

[SEAL]

Attest:

RUTH C. MASON  
Attesting Officer

C. MARSHALL DANN  
Commissioner of Patents and Trademarks